United States Patent [19]

Frenkel et al.

[11] Patent Number: 5,064,410
[45] Date of Patent: Nov. 12, 1991

[54] STRESS CONTROL SYSTEM AND METHOD

[76] Inventors: Richard E. Frenkel; Barbara G. Frenkel, both of 33 Park Rd., Scarsdale, N.Y. 10583

[21] Appl. No.: 872,143

[22] Filed: Jun. 9, 1986

Related U.S. Application Data

[63] Continuation-in-part of Ser. No. 680,888, Dec. 12, 1984, abandoned.

[51] Int. Cl.$^5$ .............................................. A61M 21/00
[52] U.S. Cl. ......................................... 600/26; 600/27
[58] Field of Search ................... 604/31, 66; 128/690, 128/734, 670, 736, 1 C, 13 R; 600/26, 27

[56] References Cited

U.S. PATENT DOCUMENTS

| 3,274,994 | 9/1966 | Storm | 128/2 |
| 3,442,263 | 5/1969 | Pascaud | 128/690 |
| 3,508,540 | 4/1970 | Cavallari et al. | 128/734 |
| 3,773,049 | 11/1973 | Rabicher et al. | 128/1 C X |
| 3,814,082 | 6/1974 | Taylor | 128/670 |
| 3,901,214 | 8/1975 | Taaffe | 128/212 |
| 3,924,606 | 12/1975 | Silva et al. | 128/21 B |
| 4,129,125 | 12/1978 | Lester et al. | 128/736 |
| 4,327,712 | 5/1982 | Frenkel et al. | 128/22 |
| 4,388,918 | 6/1983 | Filley | 128/1 C |
| 4,407,295 | 10/1983 | Skever et al. | 128/736 |
| 4,508,105 | 4/1985 | Whitten et al. | 128/1 C |
| 4,551,133 | 11/1985 | Zegers de Beyl et al. | 604/66 |

FOREIGN PATENT DOCUMENTS 3319926  12/1983  Fed. Rep. of Germany ...... 128/1 C

Primary Examiner—Lee S. Cohen
Assistant Examiner—J. P. Lacyk
Attorney, Agent, or Firm—Salzman & Levy

[57] ABSTRACT

A portable unobtrusive device to be used in combination with an imagescope. The portable device features a pair of eyeglasses having a circuit for monitoring a physiological function of the eyeglass wearer corresponding to a predetermined stress level. The circuit contains an alarm which emits an auditory and/or visual signal in response to a change in said physiological function.

14 Claims, 4 Drawing Sheets

STRESS CONTROL SYSTEM AND METHOD

RELATED APPLICATIONS

This application is a continuation-in-part of U.S. Ser. No. 680,888; filed: Dec. 12, 1984, entitled: Stress Warning Device, now abandoned and an improvement of the previously issued U.S. Pat. No. 4,327,712, issued: May 4, 1982, for: IMAGESCOPE. For purposes of brevity, the teachings set forth in the above mentioned references are meant to be incorporated herein by way of reference.

This invention relates to an unobstrusive, multi-level stress control system and method of utilizing same.

During the course of the day most individuals undergo various levels of stress. This stress in turn can cause significant and complex changes in physiological functioning. Many believe that stress which is increased beyond a certain level and which is sustained over a lengthy period of time is unhealthy. Such a stress level can be detected by changes in electrical skin conductivity, blood pressure, temperature, muscle tone and heart rate. Changes in electrical skin conductivity, will be used to measure the physiological stress in individuals for purposes of this invention.

The subject invention features a system and method which can alert users to modify their behavior before it leads them to experience dangerous levels of stress. A multi-level stress alarm is part of the inventive system, and warns of continuing increases in the levels of stress. A single stress level setting is not necessarily effective. An ordinary stress setting can cause the user to ignore the alarm. A high stress level setting can result in an individual experiencing dangerous stress before remedial action is taken. The alarm of this invention has the important advantage of being portable and unobtrusive. The stress prone person does not need to feel self conscious by the additional stress created by the observation and cognizance of his increasing stress by others.

The inventive system in its entirety comprises in combination:

1. An imagescope, described in aforementioned U.S. Pat. No. 4,327,712, for testing the particular illumination for both alleviating and treating the stressful condition in each individual.

2. An eye glass frame or other non-obtrusive portable device carried upon one's person having a built-in sensor for measuring the skin's electrical conductivity as a correlation with, and as an indication of, the stressful condition. The sensor can include a pair of sensing pads or electrodes that contact the skin. A power source provides a low current potential across the pair of sensing pads, and this potential is continiously monitored by a circuit containing a quad comparator. The quad comparator is fed a reference (battery) voltage. The reference potential is used to determine when the sensor voltage or skin resistance changes with respect to the reference voltage or resistance. Several levels of stress can be monitored by supplying several reference voltages. As the stressful level increases the skin will increase its perspiration, which in turn allows more current to flow across the sensor pads (sweat contains conductive electrolytes). Each level of stress is compared to a different reference voltage.

Upon detection of each stress level an alarm is sounded off which only the individual who is under the stress is made aware. Either of two circuits can be provided for detecting and warning the individual.

A first circuit, having a low power consumption can provide a multiple alarm level, with two distinct and discriminate alarm signals. Two or more different color LED'S can be activated in a treatment mode, wherein each color is prescriptive of the particular stress level. The prescriptive color being determined from the testing utilizing the imagescope.

The second circuit is similar to the first circuit, except that the alarm discriminates between stress levels by providing a changeable pulsating alarm as the stress level increases, thus making the individudal increasingly aware of his changing or increasing stress.

3. A peripheral apparatus for automatically medicating an invalid can be optionally attached to the eyeglass frame, and invasive delivery of a tranquilizing substance in response to a high stress signal in more extremely stressful individuals.

The method of the inventive system is as follows:
 (a) The individual is tested for calming and stress relieving colors using the imagescope;
 (b) A pair of eyeglasses is designed with lens and lighting elements such as LED'S having the color or colors obtained from the imagescope tests; and
 (c) The individual wears the eyeglasses during stressful periods, such as during working hours, in order to warn him of impending dangerous or harmful stress levels. The LED'S of the eyeglasses have a dual purpose in this regard: (1) They provide a warning of increasing stress at different levels of the stressful condition, and (2) The pulsing or flashing LED'S provide a therapeutic and calming effect, thus tending to relieve the stressful condition.

The eyeglasses of the system are unobtrusive and can be worn without alerting others that the individual is being treated for stress. The eyeglasses of the invention can be integrated into a pair of prescription or sunglasses.

The absolute levels of the physiological function at which the alarms are activated are preset by the dispensing therapist taking into account personal needs of the user as modified by trial and error. The volume of the tone can be adjusted to be audible only to the wearer.

In another embodiment, the eyeframes can contain alerting means detectable by persons other than the wearer operated by the same principle. This would be especially useful where the wearer can not be relied upon (due to physical or mental incompetency) to appropriately react to an unobtrusive signal and is under the care of a companion.

DETAILED DESCRIPTION OF THE INVENTION

Generally speaking, the invention has as one of its objects to provide an unobtrusive system and method of relieving and or reducing stress in an individual. The system of the invention comprises in the first instance, a device known as an imagescope, for determining the specific color or colors that act as stimuli in the creation of, and or the relief of, the stress condition.

Figure 3:
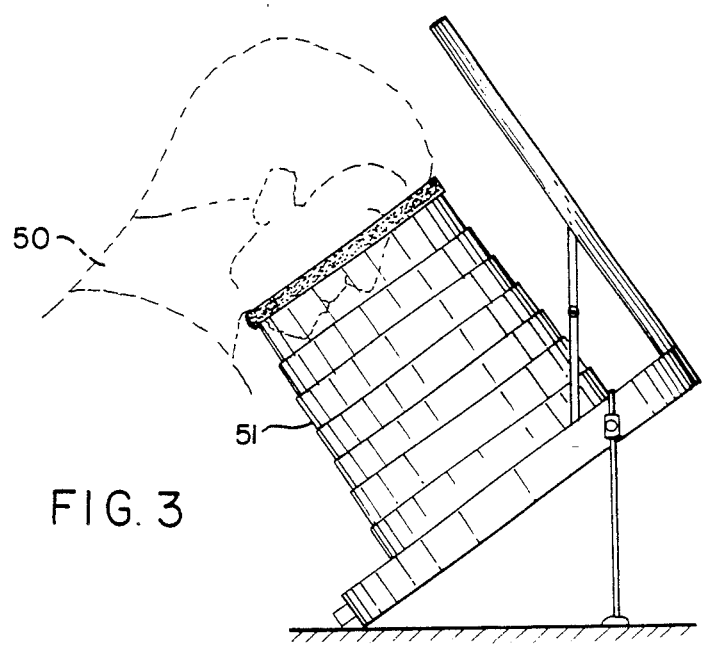
FIG. 3 is a front, in situ view of the imagescope of the inventive system.

Referring to FIG. 3, an individual 50 undergoing stress therapy, is required to gaze into the imagescope 51. The imagescope 51 generally comprises a mirrored surface (not shown) by which the individual 50 can observe his own reflection. The person's image is then bathed in different colors of light, and the therapist determines by careful analysis and questioning, the specific color or colors that effect the person's mood and stress levels.

For the sake of brevity, the teachings for the use and construction of the imagescope 51 can be obtained by way of reference to the aforementioned U.S. Pat. No. 4,327,712.

Figure 1:
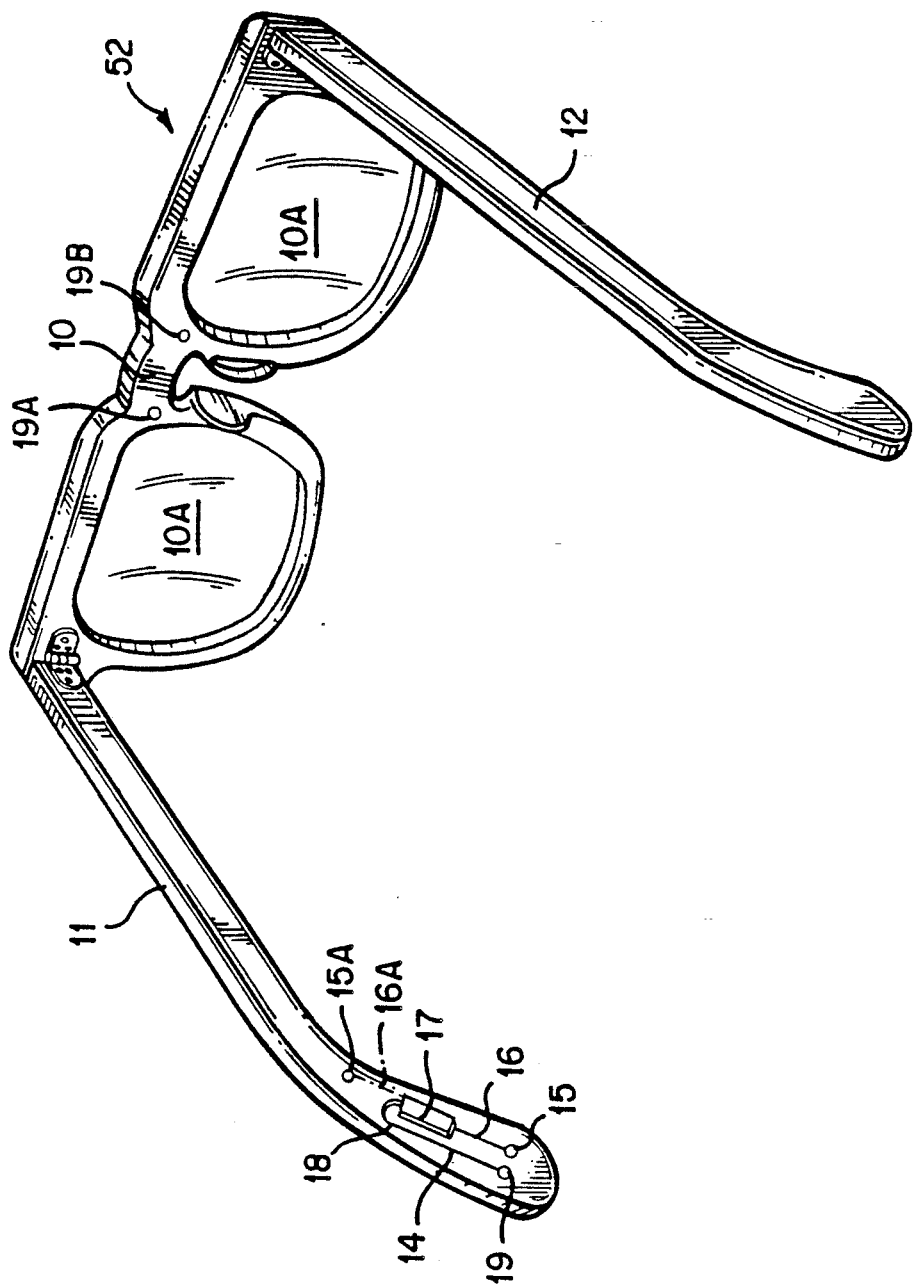
FIG. 1 is a prespective view of the eyeglasses of the inventive system.

For purposes of the present invention, the specific color which best relieves the stress or anxiety in the individual 50 is used to custom design the eyeglasses 52, illustrated in FIG. 1.

The eyeglasses 52 of FIG. 1 comprises a front section 10 and two side pieces 11 and 12. A circuit 14 (shown in more detail in FIGS. 4 and 5) for monitoring a physiological function and for providing an alarm at several given levels of stress is built into side piece 11.

Figure 2:
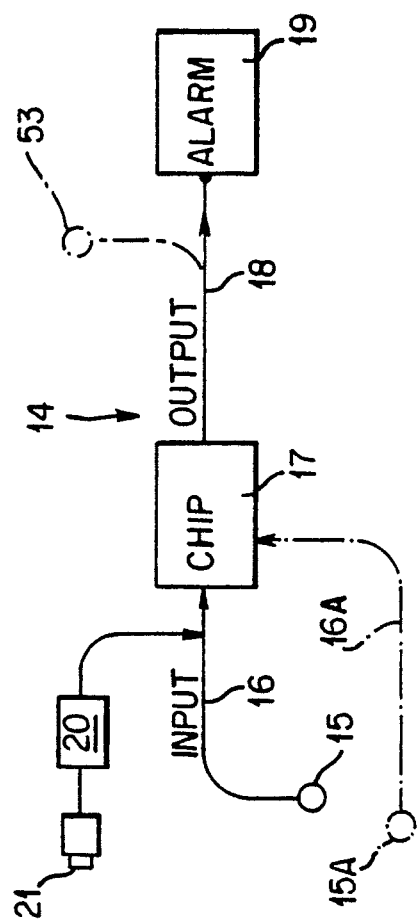
FIG. 2 is a schematic diagram of the eyeglass alarm system which is built-in to the frames shown in FIG. 1.

As shown in FIG. 2, a block diagram of the circuit 14 comprises one or more sensing devices 15, connected by one or more wires 16 to a chip-like device 17.

When the physiological function sensed by sensor 15 exceeds a first predetermined level, chip-like device 17 sends a signal to alarm 19 via wire 18, causing the alarm to emit a signal. When a second predetermined level is exceeded, a second signal is sent to alarm 19, causing the alarm to emit a second, distinct and different signal.

The preferred physiological function to be monitored is skin conductivity. There are two pads or electrodes (sensors) the first of which is designated 15 and the second of which has reference numeral 15A. The sensors are connected via lines 16 and 16A, respectively, to chip-like device 17.

The sensors or electrodes are spaced a fixed distance apart. The chip-like device 17 can be a circuit design shown in either circuit diagram of FIG. 4 or 5, which will be described in more detail, hereinafter.

Figure 4:
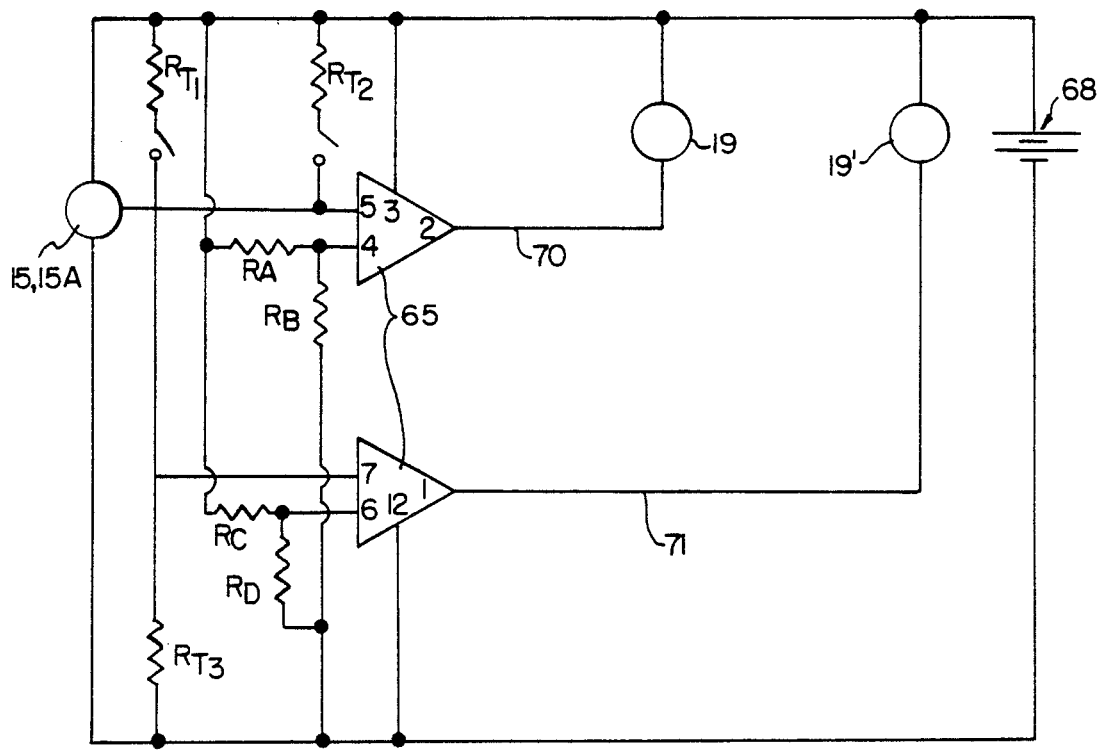
FIG. 4 is a circuit diagram for the alarm system depicted in FIG. 2.
Figure 5:
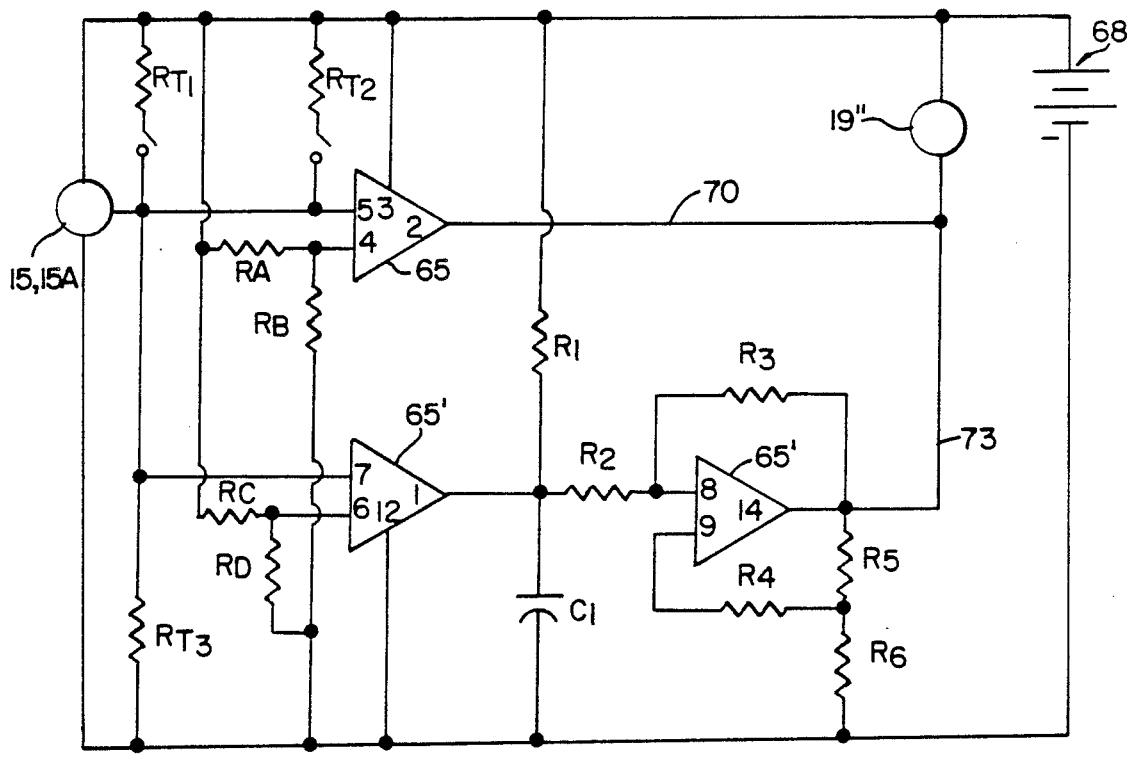
FIG. 5 is a diagram of an alternate circuit embodiment of the alarm circuit shown in FIG. 4.

Miniaturizing the circuits of FIGS. 4 and 5 into a chip-like device 17 will allow such circuits to fit into frame piece 11.

If skin temperature is to be monitored, the circuit shown in U.S. Pat. No. 3,274,994 can be used, incorporated herein by way of reference. In such case sensor 15 and 15A can be a thermocouple.

Regardless of which physiological function is monitored, the apparatus is operative to emit alarms, which are different and distinctive, in order to distinguish the stress levels.

It is preferred that an audible signal be of a low level, and located next to the wearer's ear, so that only the wearer will be cognizant of the stress level warning.

The signals can be continuous at a low level of stress identification, and pulsating at a higher stress level.

Also, the tone may have different pitch to distinguish the different stress levels.

The alarm 19 can also comprise light-emitting diodes 19A and 19B located in front 10 of the eyeglasses 52 so that only the wearer could detect their illumination. Of course, two different light emissions (steady or pulsating) could be used. This light emission could provide stress relief as well as an alarm.

It is desirable to have a test circuit 20 as part of overall circuit 14 to provide an input to the chip-like device that is equivalent to that generated by the monitored physiological function related to excess stress. Test circuit 20 can be activated by pressing button 21, which would be conviently located on the outside of side piece 11 of eyeframe 10.

It can be seen that the invention provides for the monotoring of potentially serious levels of a physiological function that is portable and unobtrusive. The patient can wear the device without embarrassment because the alarms being generated are observable only to him, and not to outsiders.

Moreover the invention provides continuous monitoring of the physiological function without conscious effort by the wearer. Merely wearing the device can be relaxing and beneficial to the wearer's peace of mind, because the absence of an alarm assures the wearer that he is not undergoing serious physiological stress. This is similar to the assurance one has when sleeping in a room having a smoke detector. The device creates a desirable biofeedback loop, i.e. when the wearer hears no alarm, he experiences no stress, so that the alarm on the device is not activated.

In an optional embodiment of the invention, the lenses of the eyeglasses 52 can be tinted various colors. It has been found that controlled color perception can generally cause a profound psychological effect for reasons described in U.S. Pat. No. 4,327,712. The coloring effect would further enhance the above-described stress-reducing effect.

Figure 6:
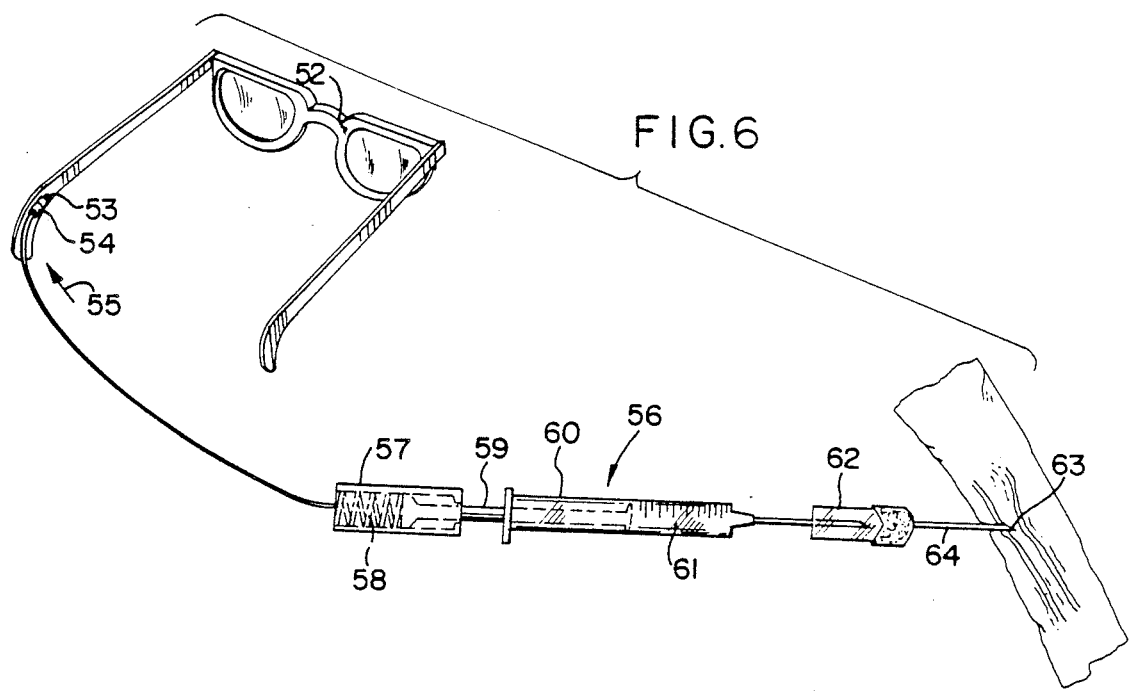
FIG. 6 is a perspective view of a self-medicating system in accordance with the inventive eyeglasses illustrated in FIG. 1.

Now referring to FIG. 6, an optional, self-medicating system is shown utilizing the eyeglasses 52 illustrated in FIG. 1. The eyeglasses 52 can comprise an output (female) jack 53 as an extension of line 18 of citcuit 14 of FIG. 2. A male plug 54 is inserted into (arrow 55) the female jack 53, in hospital patients. The plug 54 is connected to an invasive system, such as an I.V. device 56.

When a high level of stress is sensed in the individual a signal is transmitted to triggering device 57 comprising a syringe barrel and a spring-loaded switch or solenoid 58, that actuates a plunger 59 of a syringe 60. The syringe 60 contains a tranquilizing medication 61, which is forced into hep-lock 62, and hence, into the vein 63 of the patient via the vein needle 64.

Now referring to FIGS. 4 and 5, two detailed circuit embodiments are illustrated for the chip-like device 17 of FIG. 2. Each cifcuit uses several low power quad comparator IC's (RCA CA 339) hereinafter designated as circuits 65. The rest of the circuitry can be customized into these IC's or can be fabricated as additional IC's for electrical connection with circuits 65 to provide miniaturization.

For purposes of brevity the same element designations of FIG. 2 will be used where possible.

Each circuit 65 of FIG. 4 and 5 can compare two electrical signals and provide an alarm signal when one electrical imput becomes greater or lesser than the other imput signal.

One such imput signal is provided by sensor elements 15 and 15A. The other imput signal is supplied by the reference resistors $R_A$, $R_B$, $R_C$, and $R_D$ via the voltage source 68. In FIG. 4, a first alarm 19 is triggered by the first comparator circuit 65 via line 70, while a second alarm 19' is triggered by the second comparator circuit 65 via line 71.

In FIG. 5, two comparator circuits 65' are ganged to provide a pulsed signal to alarm 19" via output line 73.

The electrical source 68 is a miniaturized battery. The aforementioned resistors for setting the reference imput can be made variable, if so desired. Resistive test switches $R_{T1}$ and $R_{T2}$ are equivalent to elements 20 and 21 in FIG. 2, and are used to periodically monitor or test the system functions.

The alarms 19 and 19', respectively, of FIG. 4, are self-discriminating, i.e. each provide different LED colors and/or a different tonal signal. Obviously, each comparator is set for activation at a different stress level to provide multiple signals.

In FIG. 5, as aforementioned, the alarm 19" can provide a steady or continuous light and/or tone alarm from the first comparator 65 via line 70, or a pulsating light and/or tone signal from ganged comparators 65' via line 73.

Having thus described an exemplary form of the invention what is desired to be protected by Letters Patent is presented by the subsequently appended claims.

What is claimed is:

1. A method of controlling stress in an individual comprising the steps of:
   (a) testing the individual with an image reflecting device to determine stress associated colors for said individual;
   (b) constructing a pair of eyeglasses containing lenses having a color which is stress-calming for the tested individual;
   (c) unobtrusively carrying upon said pair of eyeglasses sensing means for determining at least two different stress levels in said individual, and alarm means connected to said sensing means for emitting two distinct signals respectively corresponding to each stress level;
   (d) wearing said eyeglasses having said sensing and alarm means by said individual; and
   (e) monitoring at least two stress levels in said individual wearing said eyeglasses, and in response to each stress level monitored, unobtrusively emitting color alarms, each respective alarm wherein only said individual is made aware of the alarms, and said alarms are stress-calming.

2. The method of claim 1, wherein said stress level is sensed by measuring a physiological change in said individual.

3. The method of claim 2, wherein the physiological change comprises a variance in the electrical conductivity of the skin.

4. The method of claim 1, wherein said emitting signal comprises an audio and visual warning observable only by the individual.

5. The method of claim 4, wherein said emitting signal comprises a pulsating warning.

6. The method of claim 1, wherein a medicating means is attached to said eyeglasses, and wherein said method further comprises the step of (f) administering a tranquilizing substance in response to the sensing of a given high level of stress.

7. The method of claim 1, wherein said warning signal has the purpose of therapeutic relief of stress.

8. A pair of stress relieving glasses comprising a frame to be worn about eyes of said individual wearer, said frames comprising means for supporting lens in said frame, said lenses being color coordinated to match a predetermined stress-relieving color particular to said individual wearer, whereby said individual will experience a calming effect when wearing said pair of stress relieving glasses.

9. For use with an image-reflecting device for determining stress-calming colors for each respective individual, the invention comprising: a pair of eyeglasses having colored lenses corresponding to a determined stress-calming color for said individual, said eyeglasses having an unobtrusive pair of alarms for signalling only to the individual two respective and distinct warnings corresponding to a minor stress level and a dangerous stress level, said alarms being self-discriminating and providing different colors to distinguish each stress level, said alarms being part of a circuit for monitoring a physiological function, said circuit having a sensor connected to each alarm, and wherein the colors emitted by said alarms are themselves stress-calming colors.

10. The eyeglasses in accordance with claim 9, wherein said monitoring circuit measures skin conductivity.

11. The eyeglasses in accordance with claim 9, wherein said monitoring circuit measures skin temperature.

12. The eyeglasses in accordance with claim 9, wherein at least one warning comprises an auditory signal.

13. The eyeglasses in accordance with claim 12, wherein said auditory signal corresponds to one of said two respective and distinct warnings.

14. The eyeglasses in accordance with claim 9, wherein one of said warnings comprises a pulsating signal.

* * * * *